United States Patent [19]

Slaugh et al.

[11] Patent Number: 4,929,584
[45] Date of Patent: May 29, 1990

[54] ALKYLATION OF BENZENE COMPOUNDS WITH DETERGENT RANGE OLEFINS

[75] Inventors: Lynn H. Slaugh, Cypress; Thomas H. Johnson; Ronald J. Hoxmeier, both of Houston, all of Tex.

[73] Assignee: Shell Oil Company, Houston, Tex.

[21] Appl. No.: 330,516

[22] Filed: Mar. 30, 1989

[51] Int. Cl.$^5$ ............................................. B01J 31/14
[52] U.S. Cl. ................................... 502/112; 502/117; 585/456
[58] Field of Search ............................... 502/112, 117

[56] References Cited

U.S. PATENT DOCUMENTS

| | | | |
|---|---|---|---|
| 3,153,677 | 10/1964 | Domash et al. | 260/671 |
| 3,261,879 | 7/1966 | Banks | 260/683 |
| 3,365,513 | 1/1968 | Heckelsberg | 260/683 |
| 3,445,541 | 4/1969 | Heckelsberg et al. | 260/683 |
| 4,358,628 | 11/1982 | Slaugh | 585/455 |
| 4,388,219 | 6/1983 | Bujadoux | 502/113 X |
| 4,826,794 | 5/1989 | Coosemans et al. | 502/110 |

*Primary Examiner*—Patrick P. Garvin

[57] ABSTRACT

This invention relates to a catalyst composition prepared by reacting in a hydrocarbon solvent a molybdenum or tungsten halide with diethylaluminumtriethylsilaneolate. Preferably the halide is tungsten hexachloride. The instant compositions are particularly useful for the alkylation of benzene and lower-alkyl benzenes with detergent range olefins.

12 Claims, No Drawings

ALKYLATION OF BENZENE COMPOUNDS WITH DETERGENT RANGE OLEFINS

FIELD OF THE INVENTION

This invention relates to catalysts and a process for alkylating benzene compounds with detergent range olefins, said catalysts comprising tungsten/molybdenum halides and a siloxyalane.

BACKGROUND OF THE INVENTION

Alkylated aromatics are important materials that have utility for several applications. For example, the so-called "linear alkyl benzenes", which are benzenes which have been alkylated with detergent range linear olefins, are useful detergent intermediates. At present, these compounds are manufactured by two different processes, namely, $AlCl_3$-catalyzed alkylation of aromatics with monochloro-paraffins and HF-catalyzed alkylation with internal olefins. In principle, advantages could result from using a less corrosive system.

U.S. Pat. No. 3,153,677 issued Oct. 20, 1964, teaches the use of supported tungsten oxide to alkylate benzene compounds with $C_2$ to $C_5$ range olefins. Tungsten oxide materials, however, are generally known as disproportionation catalyst, particularly when used in the presence of detergent-range olefins. See, for example U.S. Pat. No. 3,261,879 issued July 19, 1966; U.S. Pat. No. 3,365,513 issued Jan. 23, 1968 and U.S. Pat. No. 3,445,541 issued May 20, 1969. U.S. Pat. No. 4,358,628 discloses that certain supported tungsten oxide catalysts can be used to alkylate benzene compounds with detergent range olefins. There is no indication in the prior art that tungsten and molybdenum halides in combination with certain siloxyalanes can be utilized to alkylate benzene compounds with detergent range olefins.

SUMMARY OF THE INVENTION

This invention relates to a catalyst composition prepared by reacting in a hydrocarbon solvent a molybdenum or tungsten halide with a siloxyalane of the formula $(CH_3CH_2)_3SiOAl(CH_3CH_2)_2$, also referred to herein as diethylaluminumtriethylsilaneolate. The instant compositions are particularly useful as alkyation catalysts, particularly catalysts for the alkylation of benzene compounds with detergent range olefins. The tungsten and molybdenum halides alone have no alkylation activity.

DETAILED DESCRIPTION OF THE INVENTION

Catalyst Composition

The catalyst composition comprises the produce of contacting in a hydrocarbon solvent a molybdenum halide or a tungsten halide and a siloxyalane of the formula $(CH_3CH_2)_3SiOAl(CH_3CH_2)_2$, also referred to herein as diethylaluminumtriethylsilaneolate.

Suitable molybdenum and tungsten halides are those wherein the halogen is of atomic number from 9 to 53 inclusive, e.g., fluorine, chlorine, bromine and iodine. Illustrative molybdenum halides are molybdenum tetrabromide, molybdenum pentachloride and molybdenum hexafluoride and illustrative tungsten halides are tungsten tetriodide, tungsten pentabromide and tungsten hexachloride. The halide of molybdenum or tungsten is preferably combined with the siloxyalane in a high positive oxidation state, e.g., molybdenum pentahalide or tungsten hexahalide. Particularly preferred for preparation of the catalyst composition are molybdenum and tungsten chlorides, especially molybdenum pentachloride and tungsten hexachloride, with the latter being the most preferred species.

The compositions are prepared by reacting a heavy metal halide, that is a molybdenum or tungsten halide with the siloxyalane in the presence of a hydrocarbon solvent. The hydrocarbon solvent is generally hydrocarbyl in nature, that is, consisting of hydrogen and carbon and, optionally, substituents, such as halo, etc., that are inert to the reactants may be present on the solvent molecule. Oxygen containing substituents such as hydroxy, alkoxy, keto, carboalkoxy, nitro, etc., are detrimental. The solvent should be substantially water-free. Suitable solvents include the acyclic and cyclic alkanes and the benzenes. Non-limiting illustrative examples include hexane, heptane, dodecane, cyclohexane, cyclopentane, 3-chlorohexane, 1-chlorooctane, chlorocyclohexane, chlorocyclopentane, chlorobenzene, benzene, toluene, the xylenes, etc. The olefin feed stock can also be suitably used as a solvent.

The molar ratio of heavy metal halide to siloxyalane will typically range from about 10:1 to about 1:10, preferably from about 5:1 to about 1:5, and more preferably from about 2:1 to about 1:2.

The catalyst preparation reaction should be carried out under substantially anhydrous and oxygen-free conditions. Reaction temperatures are not critical and will typically range from about 0° C. to alkylation reaction conditions. Preferred reaction temperatures range from about 0° C. to about 50° C. While it is generally preferred to separately prepare the catalyst and then add to it the olefin feedstock under alkylation conditions, the catalyst can be prepared in situ in the alkyation reactor at alkylation conditions in the presence of the olefin feedstock.

The Process

The aromatic compound to be alkylated by the process of the instant invention is benzene or a substituted benzene, preferably an alkyl-substituted benzene. Of the alkyl-substituted benzenes, particularly desirable are the mono- and poly-substituted lower alky benzenes, wherein the substituted alkyl substituent has a carbon number ranging from about 1 to about 5, more particularly ranging from 1 to about 2. Suitable examples include the following as particularly desirable alkylation feedstocks: benzene, toluene, xylenes, ethylbenzene, cumene, n-propylbenzene and other mono- and poly-lower alkyl benzenes. Particularly desirable are benzene, toluene and xylene. The aromatic feedstock can be a single aromatic hydrocarbon or a mixture of two or more aromatic hydrocarbons. The aromatic hydrocarbons can be fed into the reactor neat or mixed in a suitable non-reactive organic solvent such as for example a saturated hydrocarbon.

The olefins employed in the alkylation reaction are olefins in the so-called detergent range, i.e., having carbon numbers ranging from about 8 to about 22, preferably from about 10 to about 20. The olefins may be alpha or internal and may be either straight chain or branched chain olefins. The olefin feedstock can be either a highly purified olefin or a mixture of two or more olefins or a fraction rich in one or more of the olefins and containing also paraffins or other hydrocarbons of similar boiling range.

In operation, the catalyst is contacted with the benzene to be alkylated and the olefin to be utilized for alkylation at a temperature between about −10° C. to about 350° C. Temperatures between about 0° C. and about 200° C. are very suitable, while temperatures between about 0° C. and about 75° C. are preferred, and temperatures between about 0° C. and about 50° C. are particularly preferred. Pressures are not critical. Typical pressures will range from about atmospheric to about 2000 psig. An aromatic to olefin molar ratio of about 10:1 to about 20:1, preferably from about 2:1 to about 15:1 can be employed.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The following examples are provided for illustration purposes and are not to be construed as limiting the invention.

ILLUSTRATIVE EMBODIMENTS

EXAMPLE 1: Preparation of Diethylaluminumtriethylsilaneolate

In a flask, under a dry inert atmosphere, were placed 2.3 grams (20 mmoles) of triethylaluminum (25% wt. heptane solution) and 22.2 grams of dry toluene. While mechanically stirring the contents, 2.64 grams (20 mmoles) of triethylsilanol dissolved in 8 grams of toluene were added dropwise via a syringe over a period of thirty minutes while the temperature was maintained at 20°–35° C. The syringe was rinsed with an additional 8 grams of toluene and the latter solution added to the reaction mixture. After stirring for an additional one-half hour, no more gas evolution was detected, and the product solution was store in a sealed bottle inside a drybox. A $^{13}C$ NMR analysis showed diethylaluminumtriethylsilaneolate to be the major product component. All triethylsilanol had reacted.

Alkylation Reactions

The alkyation reactions were all performed in a Vacuum Atomspheres dry box maintained under a dry nitrogen atmosphere. Reaction analysis was performed by gas chromatography with product identification done by mass spectrometry. All solvents and organic reactants were dried over molecular sieves and purged with nitrogen prior to use. Tungsten hexachloride was subjected to sublimation prior to use to rid it of various tungsten oxides.

EXAMPLE 2: Alkylation with WCl$_6$/diethylaluminumtriethylsilaneolate

To a 250-ml Erlenmeyer flask were added 150 ml of chlorobenzene, 1.25 mmoles of WCl$_6$ and 1.6 mmoles of the diethylaluminumtriethylsilaneolate from Example 1. The mixture was stirred for 15 minutes at room temperature. Then, an 11/110, mmoles/mmoles mixture of isomerized n-decene and toluene were added to the reation flask. Stirring was continued at room temperature for 18 hours. Analysis of the solution revealed that all of the decene had been consumed to a mixture of decyltoluene isomers. A trace amount of dodecyltoluene isomers were observed. No metathesis products of decene or of the alkylates were observed.

Illustrative Embodiment

When catalysts are prepared with MoCl$_5$ and the siloxyalane of Example 1 are tested under alkylation conditions similar to that of Example 2, product analysis will indicate the presence of alkylation products.

COMPARATIVE EXAMPLE 3

To a 250-ml Erlenmeyer flask were added 150 ml of chlorobenzene and 1.25 mmoles of WCl$_6$. The mixture was stirred for 15 minutes at room temperature. Then, an 11/110, mmoles/mmoles mixture of isomerized decene and toluene were added to the reaction flask. Stirring was continued at room temperature for 18 hours. Analysis of the solution revealed no metathesis or alkylation had occurred.

COMPARATIVE EXAMPLE 4: Alkylation with WCl$_6$/dimethylaluminumtriethylsilaneolate To a 250-ml Erlenmeyer flask were added 150 ml of chlorobenzene, 1.25 mmoles of WCl$_6$ and 1.6 mmoles of the dimethylaluminumtriethylsilaneolate prepared in the same manner as the diethyl analog in Example 1. The mixture was stirred for 15 minutes at room temperature. Then, an 11/110, mmoles/mmoles mixture of isomerized n-decene and toluene were added to the reaction flask. Stirring was continued at room temperature for 18 hours. Analysis of the solution revealed only a trace amount of decyltoluene isomers present and no metathesis products of decene or of their alkylates were observed.

I claim as my invention:

1. A catalyst composition prepared by reacting in a hydrocarbon solvent a molybdenum or tungsten halide with diethylaluminumtriethylsilaneolate.

2. The catalyst of claim 1 wherein the halide is selected from chloride, bromide and iodide.

3. The catalyst of claim 2 wherein the halide is chloride.

4. The catalyst of claim 3 wherein the halide is tungsten halide.

5. The catalyst of claim 4 wherein the halide is tungsten hexachloride.

6. The catalyst of claim 1 wherein the molar ratio of molybdenum or tungsten halide to diethylaluminumtriethylsilaneolate ranges from about 1:10 to about 10:1.

7. The catalyst of claim 6 wherein the molar ratio of molybdenum or tungsten halide to diethylaluminumtriethylsilaneolate ranges from about 1:5 to about 5:1.

8. The catalyst of claim 7 wherein the molar ratio of molybdenum or tungsten halide to diethylaluminumtriethylsilaneolate ranges from about 1:2 to about 2:1.

9. The catalyst of claim 5 wherein the molar ratio of tungsten halide to diethylaluminumtriethylsilaneolate ranges from about 1:10 to about 10:1.

10. The catalyst of claim 9 wherein the molar ratio of tungsten halide to diethylaluminumtriethylsilaneolate ranges from about 1:5 to about 5:1.

11. The catalyst of claim 10 wherein the molar ratio of tungsten halide to diethylaluminumtriethylsilaneolate ranges from about 1:2 to about 2:1.

12. The catalyst of claim 1 wherein the reaction is carried out at a temperature ranging from 0° C. to about 50° C.